United States Patent [19]

Kleemann et al.

[11] 4,424,370
[45] Jan. 3, 1984

[54] CYCLIC ACETALS OF N-ACYLGLUTAMIC ACID-γ-SEMIALDEHYDES, PROCESS FOR THEIR PRODUCTION AND USE

[75] Inventors: Axel Kleemann; Marc Samson, both of Hanau, Fed. Rep. of Germany

[73] Assignee: Degussa Aktiengesellschaft, Frankfurt, Fed. Rep. of Germany

[21] Appl. No.: 320,129

[22] Filed: Nov. 10, 1981

[30] Foreign Application Priority Data

Nov. 15, 1980 [DE] Fed. Rep. of Germany ....... 3043252

[51] Int. Cl.³ .......................................... C07D 317/30
[52] U.S. Cl. ................................... 549/373; 549/452; 548/309
[58] Field of Search ................ 549/373, 452; 560/160, 560/170

[56] References Cited

U.S. PATENT DOCUMENTS 3,787,471 1/1974 Harris et al. ......................... 549/452
4,376,864 3/1983 Drauz et al. ......................... 549/373

FOREIGN PATENT DOCUMENTS 1816703 7/1969 Fed. Rep. of Germany ...... 560/170
2011917 9/1971 Fed. Rep. of Germany ...... 560/170

*Primary Examiner*—Ethel G. Love
*Attorney, Agent, or Firm*—Cushman, Darby & Cushman

[57] ABSTRACT

The invention is directed to a cyclic acetal of N-acylglutamic acid-γ-semialdehyde of the formula

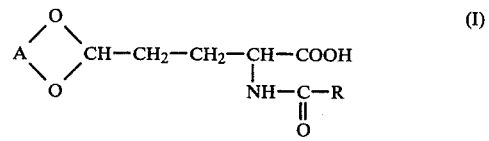 (I)

in which A is an unsubstituted alkylene group having 2 to 3 carbon atoms or such an alkylene group substituted by 1 to 2 methyl groups and R is a methyl, methoxy, phenyl, or benzyloxy group and to a method of producing a compound of formula (I) by reaction of a compound of the general formula

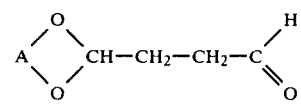

in which A is as defined above, with hydrogen cyanide or a cyanide ion supplying compound, ammonia or an ammonium ion supplying compound and carbon dioxide or a carbonate ion supplying compound and basic hydrolysis of the reaction mixture obtained and reaction of the hydrolysis mixture with a suitable acylating compound and use of the compounds of formula (I) to produce α-N-acyltryptophane.

5 Claims, No Drawings

CYCLIC ACETALS OF N-ACYLGLUTAMIC ACID-γ-SEMIALDEHYDES, PROCESS FOR THEIR PRODUCTION AND USE

SUMMARY OF THE INVENTION

The present invention is directed to a cyclic acetal of N-acylglutamic acid-γ-semialdehyde of the formula

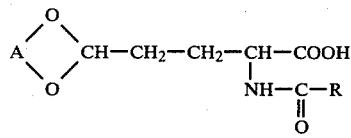 (I)

in which A is an unsubstituted alkylene group having 2 to 3 carbon atoms or such an alkylene group substituted by 1 to 2 methyl groups and R is a methyl, methoxy, phenyl, or benzyloxy group and to a method of producing a compound of formula (I) by reaction of a compound of the general formula

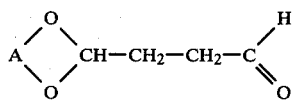 (II)

in which A is as defined above with hydrogen cyanide or a cyanide ion supplying compound, ammonia or an ammonium ion supplying compound and carbon dioxide or a carbonate ion supplying compound, a basic hydrolysis of the reaction mixture obtained, and acetylation of the hydrolysis mixture.

These cyclic acetals of N-acylglutamic acid-γ-semialdehydes are valuable intermediates for the production of the corresponding N-acyltryptophane. A further object of the invention therefore is the use of the products to produce the corresponding N-acyltryptophane.

L-tryptophane is an essential aminoacid which frequently represents the limiting aminoacid in fodders and mixed fodders. Since L-tryptophane can be obtained by the enzymatic splitting of D,L-N-acyl-tryptophanes, their synthesis has great significance.

The cyclic acetals of N-acylglutamic acid-γ-semialdehyde of the general formula (I) can be produced by a process comprising (a) reacting a compound of the general formula

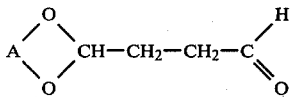 (II)

in which A is as defined above in a aqueous or aqueous-alcoholic solution with hydrogen cyanide or a cyanide ion supplying compound, ammonia or an ammonium ion supplying compound and carbon dioxide or a carbonate ion supplying compound and (b) hydrolyzing the reaction mixture obtained in step (a) under basic conditions and (c) reacting the hydrolysis mixture obtained in step (b) with a suitable acylating compound.

The three reaction steps (a), (b), and (c) of the process of the invention proceed with high conversion.

Since the compounds employed of general formula (II) are also obtainable through hydroformylation of the corresponding 2-vinyl-1,3-dioxolane or 2-vinyl-1,3-dioxane and the latter are easily obtainable in high yields by acetalisation of acrolein with the corresponding 1,2-glycol or 1,3-glycol, the cyclic acetals of N-acylglutamic acid-γ-semialdehydes of the general formula I can be produced economically. Since the compounds of general formula (I), likewise then can be changed into the corresponding N-acyltryptophane of the general formula

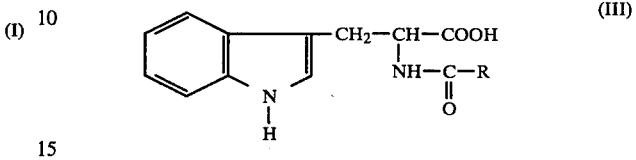 (III)

in which R is again as defined above, easily and with high yields there is overall opened up a new advantageous, economical manner starting from acrolein to form these N-acyltryptophanes and therewith to form L-tryptophane.

Examples of the compounds employed of general formula (II) are 2-(2'-formylethyl)-1,3-dioxolane, 2-(2'-formylethyl)-1,3-dioxane or 2-(2'-formylethyl)-5,5-dimethyl-1,3-dioxane.

The compounds of general formula (II) are reacted in a first reaction step which is known in itself for the formation of hydantoins from aldehydes with hydrogen cyanide or a cyanide ion supplying compound, such as sodium cyanide or potassium cyanide with ammonia or an ammonium ion supplying compound, such as ammonium hydroxide or ammonium chloride, and with carbon dioxide or a carbonate ion supplying compound, such as sodium or potassium carbonate, sodium or potassium bicarbonate, or sodium or potassium carbamate. There can also be employed compounds which simultaneously supply cyanide and ammonium ions, such as ammonium-cyanide, or which simultaneously supply ammonium and carbonate ions, such as ammonium carbonate, or ammonium carbamate.

The reaction in the first reaction step takes place in water or in a mixture of water and methanol or ethanol. It can be undertaken in a wide temperature range. Preferably there is employed a temperature between 30° and 90° C., because in this range a satisfactory reaction speed is attained and the perhaps necessary superatmospheric pressure does not create an industrial obstacle.

The amounts of the individual reactants can be varied within a wide range. Preferably per mole of compound of general formula (II) there is employed 1 to 1.5 moles of hydrogen cyanide or cyanide ion supplying compound, 2 to 15 moles of ammonia or an ammonium ion supplying compound and 1 to 2 moles of carbon dioxide or a carbonate ion supplying compound. The compounds of general formula (II) can be reacted simultaneously with all three other reactants. However, it is likewise also possible to first react them with the cyanide component and subsequently react simultaneously with the two other components, or first to react them only with the cyanide component, then react only with the ammonium component and only after that react with the carbon dioxide of carbonate component. It is especially advantageous to have the compound of general formula (II) dissolved in methanol or ethanol and to slowly feed this solution into an aqueous solution or suspension of the other reactants at the desired reaction temperature. To achieve high conversions there is recommended a suitable post reaction time of for example, 5 hours after the end of the feeding in.

Depending on the reaction conditions used the reaction mixture after carrying out the first reaction step contains besides the expected hydantoin of the general formula

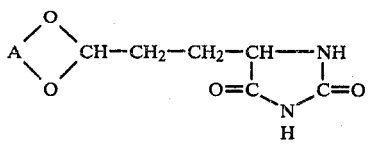
(IV)

also a more or less large portion of the α-N-carbamoyl-carboxylic acid amide of the general formula

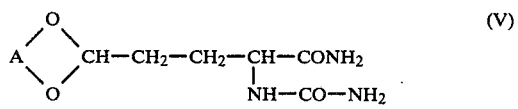
(V)

wherein in formula (IV) and (V) A is again as defined above.

However, it is not necessary to separate the two reaction products, since both of them are reacted in subsequent reaction step (b) to the cyclic acetals of glutamic acid-γ-semialdehyde. However, it can be suitable before carrying out the second reaction step (b) to remove the ammonium salts contained in the crude reaction mixture of the first reaction step (a) by heating, to distill off the optionally present alcohol and to concentrate the reaction mixture under reduced pressure.

Then the mixture of compounds of general formula (IV) and (V) obtained in step (a) are reacted under basic hydrolysis conditions for forming the α-aminoacids from the corresponding substituted hydantoins in a manner known of itself. Preferably there are used alkali or alkaline earth metal hydroxides or alkaline metal carbonates in aqueous medium. For example, there can be used with good success NaOH, KOH, Na$_2$CO$_3$, K$_2$CO$_3$, Ca(OH)$_2$ or Ba(OH)$_2$. The reaction temperature can be varied in a wide range between 20° C. and 200° C. Preferred are temperatures between 100° C. and 150° C. since in this range satisfactory reaction speeds can be attained. Especially preferred saponification conditions are temperatures between 130° C. and 150° C., reaction times of 0.5 to 1 hour and a mole ratio of substrate to base of 1:2.2.

The hydrolysis mixture after carrying out process step (b) contains an aqueous solution of the corresponding salt of glutamic acid-γ-semialdehyde-acetal. This hydrolysis mixture can be employed directly for process step (c). However, it can be suitable before carrying out the third reaction step to remove ammonia which is dissolved in the crude hydrolysis mixture by heating at normal pressure or in a vacuum.

In reaction step (c) the aqueous solution of glutamic acid-γ-semialdehyde-acetal obtained in step (b) is reacted with suitable acylating agents. Examples of the acylating agents employed in aqueous medium are acetyl chloride, acetic anhydride, methyl chloroformate, benzoyl chloride, or benzyloxycarbonyl chloride. Similarly there can be used for example acetyl bromide, benzoyl bromide, benzyloxycarbonyl bromide.

Reaction step (c) is suitably carried out at a pH above 7. Depending on the carrying out of reaction step (b) it can be necessary to adjust the pH by addition of base during the reaction. The reaction temperature can be varied within wide limits. Suitable are temperatures between 0° and 80° C., preferably between 0° and 25° C. The acylating reagents can be employed in excess. However, for economical reasons it is more advantageous to only employ the amount equivalent to the amount of compound of general formula (II) in reaction step (a).

The acylating agents can be added all at once to the mixture obtained from reaction step (b). However, it is more advantageous to slowly feed the acylating reagents into the mixture obtained from reaction step (b). In both cases, a reaction time of about 1 hour totally is generally sufficient.

Since the cyclic acetals of N-acylglutamic acid-γ-semialdehyde formed are nearly all difficultly soluble in water at room temperature, they can be isolated by a simple filtration and in high purity.

In order to produce N-acyl-tryptophane from the N-acylglutamic acid-γ-semialdehyde-acetals they are reacted at a pH between 0.1 and 4, preferably between 1 and 3, with phenylhydrazine. The required pH can be established by an inorganic acid such as sulfuric acid or phosphoric acid, by an organic acid such as oxalic acid, formic acid, acetic acid, benzenesulfonic acid or p-toluenesulfonic acid or by a strongly acid ion exchanger, e.g. a sulfonated styrene-divinyl benzene resin. Preferably there is used hydrochloric acid.

The reaction temperature can be varied within wide limits. Suitable are temperatures between 60° and 150° C., preferably between 70° and 120° C.

The phenylhydrazine can be employed in excess. However, for economical reasons it is more advantageous to only use the amount which is equivalent to the N-acylglutamic acid-γ-semialdehyde-acetal employed.

The phenylhydrazine can be mixed with the N-acylglutamic acid-γ-semialdehyde-acetal and the necessary amount of acid and be heated to the desired reaction temperature. However, it is likewise also possible to have present an acid solution of the phenylhydrazine, to heat, and feed in a solution of N-acylglutamic acid-γ-semialdehyde-acetal. In both cases a reaction time in all of 3 to 4 hours is generally sufficient. After the end of the reaction the solution of the N-acyltryptophane obtained can be concentrated and the residue recrystallized. However, the N-acyltryptophane can also be crystallized by cooling the reaction mixture, and isolated by filtration.

The invention is explained further in the following examples. Unless otherwise indicated all percentages are by weight.

The process can comprise, consist essentially of, or consist of the stated steps with the recited materials.

DETAILED DESCRIPTION

EXAMPLE 1

16.3 grams of 2-(2'-formylethyl)-1,3-dioxolane were dropped into a suspension of 48 grams of ammonium carbonate, 5.1 grams of hydrocyanic acid and 110 ml of aqueous ammonia (25%) at 35° C. in the course of one hour, and the mixture was further stirred for five hours at 40° C. Subsequently the salts were boiled out by increasing the temperature (up to 100° C. head temperature). The remaining aqueous solution was treated with 11.9 grams of sodium hydroxide and heated for 45 minutes at 140° C.

After cooling down the reaction solution was briefly concentrated in vacuum and treated within 30 minutes at 0° to 5° C. with 48.9 ml of a 50% solution of benzyl chloroformate in toluene. After further stirring for 30 minutes the solution was adjusted to pH 2 with concentrated hydrochloric acid, whereby a colorless oil separated, which upon being allowed to stand, slowly crystallized. The crystals were filtered off, then washed with water and dried in a vacuum. By recrystallization from benzene there were obtained 24.2 grams of N-benzyloxycarbonylglutamic acid-γ-semialdehyde-ethyleneacetal.

| Elemental analysis: $C_{15}H_{19}NO_6$ | | |
|---|---|---|
| Calculated C 58,24% | H 6,19% | N 4,53% |
| Found C 58,80% | H 6,11% | N 4,56% |
| $^1$H—NMR-Spectrum (CDCl$_3$): | | |

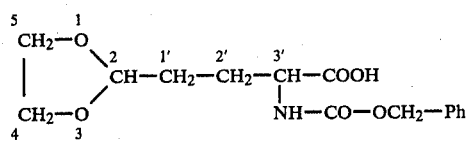

$\delta = 1,6-2,1$ (m,4H): H-1',H-2'
$\delta = 3,85$ (m,4H): H-4, H-5
$\delta = 4,4$ (m,1H): H-3'
$\delta = 4,9$ (t,1H): H-2
$\delta = 5,1$ (s,2H): -OC$\underline{H}_2$-
$\delta = 5,6$ (d,1H): N$\underline{H}$
$\delta = 7,35$ (s,5H): Aromatic H's
$\delta = 10,3$ (s,1H): COO$\underline{H}$

EXAMPLE 2

16.3 grams of 2-(2'-formylethyl)-1,3-dioxolane were dropped into a suspension of 45 grams of ammonium carbonate, 5.1 grams of hydrocyanic acid and 100 ml of aqueous ammonia (25%) at 40° C. in the course of one hour, and the mixture was stirred for a further five hours at this temperature. Subsequently the salts were boiled off by increasing this temperature (up to 100° C. head temperature). The remaining aqueous solution was treated with 15.4 grams of potassium hydroxide and heated for 50 minutes at 150° C. After cooling the reaction mixture was briefly concentrated in vacuum and treated within 40 minutes at 50° C. with 18 grams of benzoyl chloride. After 30 minutes further stirring the solution was adjusted to pH 2 with concentrated hydrochloric acid, whereby crystals separated out. The precipitate was filtered off, washed with water and dried in vacuum. By recrystallisation from benzene there were obtained 31.8 grams of N-benzoyl glutamic acid-γ-semialdehyde-ethylene acetal (Melting point 136°–137° C.).

| Elemental analysis: $C_{14}H_{17}NO_5$ | | |
|---|---|---|
| Calculated C 60,21% | H 6,13% | N 5,02% |
| Found C 59,72% | H 6,03% | N 4,98% |
| $^1$H—NMR—Spectrum (DMSO—d$_6$/CDCl$_3$) | | |

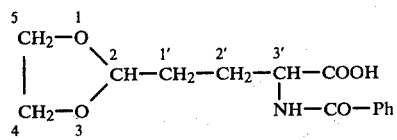

$\delta = 1,7-2,3$ (m,4H): H-1', H-2'
$\delta = 3,9$ (m,4H): H-4, H-5
$\delta = 4,65$ (m,1H): H-3'
$\delta = 4,85$ (t,1H): H-2
$\delta = 7,4$; 7,9 (m,5H): Aromatic H's
$\delta = 7,9$ (d,1H): N$\underline{H}$

EXAMPLE 3

6.5 grams of 2-(2'-formylethyl)-1,3-dioxolane were dropped into a suspension of 18 grams of ammonium carbonate, 2.0 grams of hydrocyanic acid and 40 ml of aqueous ammonia (25%) at 40° C. in the course of one-half hour and the mixture was further stirred for three hours at 55° C. Subsequently the salts were boiled off by increasing the temperature (up to 100° C. head temperature). The remaining aqueous solution was treated with 4.7 grams of sodium hydroxide and heated at 140° C. for 45 minutes. After cooling the reaction mixture was briefly concentrated in vacuum and treated within 30 minutes at 5° C. with 7 ml of acetic anhydride. After 30 minutes further stirring the solution was adjusted to pH 2 with concentrated hydrochloric acid. The reaction mixture was concentrated in vacuum and treated with 150 ml of ethanol. The insoluble salts were filtered off and the filtrate concentrated and dried in vacuum. There were obtained 7.5 grams of N-acetylglutamic acid-γ-semialdehyde-ethylene acetal.

| Elemental Analysis $C_9H_{15}NO_5$ | | |
|---|---|---|
| Calculated C 49,8% | H 6,9% | N 6,5% |
| Found C 49,7% | H 6,8% | N 6.6% |
| $^1$H—NMR-Spectrum (DMSO—d$_6$/CDCl$_3$) | | |

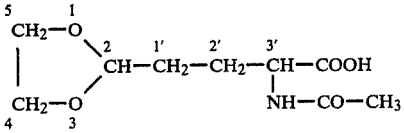

$\delta = 1,5-2,1$ (m,4H): H-1', H-2'.
$\delta = 1,95$ (s,3H): Acetyl
$\delta = 3,8$ (m,4H): H-4, H-5
$\delta = 4,2$ (m,1H): H-3'
$\delta = 4,8$ (t,1H): H-2
$\delta = 7,6$ (d,1H): N$\underline{H}$  $\delta = 12,2$ (bs,1H): COO$\underline{H}$

EXAMPLE 4

20.7 grams of 2-(2'-formylethyl)-1,3-dioxane dissolved in 50 ml of methanol were dropped into a suspension of 42 grams ammonium carbonate, 6 grams of hydrocyanic acid and 120 ml of aqueous ammonia (25%) at 50° C. in the course of one hour after which the temperature was held for another three hours at 50° C. Subsequently the methanol was distilled off and the ammonium salt boiled off at a head temperature up to 100° C. The remaining aqueous solution was treated with 11.5 grams of sodium hydroxide and heated at 160° C. for 40 minutes. After cooling, the reaction mixture was concentrated briefly in vacuum and treated with 20 ml of acetic anhydride at 5° C. After 30 minutes post reaction, the solution was adjusted to pH 2 with concentrated hydrochloric acid and extracted twice, each time with 120 ml of chloroform. The organic phase was dried over sodium sulfate, filtered, and concentrated. The residue obtained was recrystallized from benzene. Yield 24.3 grams (Melting Point: 133°–134° C.).

| Elemental Analysis $C_{10}H_{17}NO_5$ | | | |
|---|---|---|---|
| Calculated | C 51,94% | H 7,41% | N 6,06% |
| Found | C 52,45% | H 7,28% | N 6,03% |
| $^1$H—NMR-Spectrum (DMSO—$d_6$/CDCl$_3$) | | | |

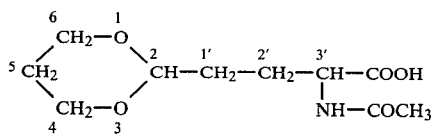

δ=1,20–2,0 (m,6H): H-1', H-2', H-5
δ=1,85 (s,3H): Acetyl
δ=3,5–4,2 (m,5H): H-4, H-6, H-3'
δ=4,45 (t,1H): H-2
δ=8,0 (d,1H): N<u>H</u>   δ=11,4 (bs,1H): COO<u>H</u>

EXAMPLE 5

A solution of 10.4 grams of 2-(2'-formylethyl)-1,3-dioxane in 40 ml of methanol was dropped into a suspension of 21 grams of ammonium carbonate, 3 grams of hydrocyanic acid and 70 ml of aqueous ammonia (25%) in the course of one hour and the mixture was stirred for a further three hours at 50° C. Subsequently the methanol was distilled off and the salts boiled off. The remaining aqueous solution was treated with 9.3 grams of potassium hydroxide and heated at 150° C. for 45 minutes. After cooling the reaction mixture was briefly concentrated in vacuum and treated dropwise with 10.2 grams of benzoyl chloride at 10° C. After 30 minutes further reaction the solution was adjusted to pH 2 with concentrated hydrochloric acid, whereby a white precipitate formed. The precipitate was filtered off, washed with water and dried in vacuum. Recrystallisation from benzene yielded 18.7 grams of N-benzoyl-glutamic acid-γ-semialdehyde-propylene-1,3-acetal (Melting Point: 157°–159° C.).

| Elemental Analysis $C_{15}H_{19}NO_5$ | | | |
|---|---|---|---|
| Calculated | C 61,42% | H 6,53% | N 4,78% |
| Found | C 61,31% | H 6,41% | N 4,73% |
| $^1$H—NMR—Spectrum (DMSO—$d_6$/CDCl$_3$) | | | |

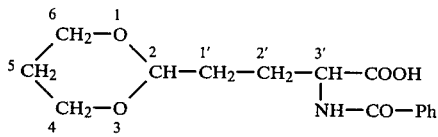

δ=1,2–2,2 (m,6H): H-1', H-2', H-5
δ=3,4–4,2 (m,4H): H-4, H-6
δ=4,4 (m,1H): H-3'
δ=7,45; 7,8 (m,5H): Aromatic H's
δ=8,5 (d,1H): N<u>H</u>
δ=10,7 (s,1H): COO<u>H</u>

EXAMPLE 6

17.2 grams of 2-2('-formylethyl)-5,5-dimethyl-1,3-dioxane, dissolved in 50 ml of methanol, were dropped into a suspension of 20 grams of ammonium carbonate, 4.8 ml of liquid hydrocyanic acid and 110 ml of aqueous ammonia (25%) at 40° C. in the course of one hour whereupon the temperature was held at 40° C. for 5 hours. Subsequently the methanol was distilled off and the ammonium salts were boiled off by further heating at 100° C. The remaining aqueous suspension was treated with 9 grams of sodium hydroxide and heated for 40 minutes at 160° C. After cooling the reaction mixture was briefly concentrated in vacuum and treated at 5° C. dropwise with 11.2 grams of acetic anhydride, after which it was stirred for a further 30 minutes. The solution was adjusted to pH 2 with concentrated hydrochloric acid, whereupon a white precipitate formed. The precipitate was filtered off, washed with water and dried in a vacuum. Recrystallization from benzene yielded 24.2 grams of N-acetylglutamic acid-γ-semialdehyde-2,2-dimethylpropylene-1,3-acetal (Melting Point: 168°–169° C.).

| Elemental Analysis $C_{12}H_{21}NO_5$ | | | |
|---|---|---|---|
| Calculated | C 55,58% | H 8,16% | N 5,40% |
| Found | C 55,91% | H 8,30% | N 5,35% |
| $^1$H—NMR-Spectrum (DMSO—$d_6$/CDCl$_3$) | | | |

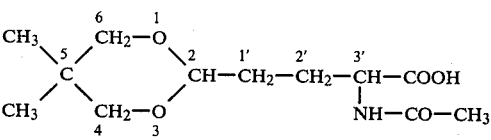

δ=0,7 (s,3H): 5-CH$_3$
δ=1,15 (s,3H): 5-CH$_3$
δ1,5–2 (m,4H): H-1', H-2'
δ=1,92 (s,3H): Acetyl
δ=3,5 (q,4H): H-4, H-6
δ=4,2–4,6 (m,2H): H-2, H-3'
δ=7,7 (d,1H): N<u>H</u>
δ=11,2 (bs,1H): COO<u>H</u>

EXAMPLE 7

In a manner analogous to Example 6 there were reacted 17.2 grams of 2-(2'-formylethyl)-5,5-dimethyl-1,3-dioxane. Instead of acetic anhydride there was used 14.1 grams of benzoyl chloride. Recrystallization from benzene yielded 31 grams of N-benzoylglutamic acid-γ-semialdehyde-2,2-dimethylpropylene-1,3-acetal (Melting Point: 193°–194° C.).

| Elemental Analysis $C_{17}H_{23}NO_5$ | | | |
|---|---|---|---|
| Calculated | C 63,53% | H 7,21% | N 4,36% |
| Found | C 63,11% | H 6,99% | N 4,28% |
| $^1$H—NMR—Spectrum (DMSO—$d_6$/CDCl$_3$) | | | |

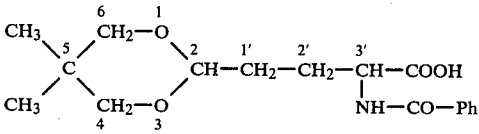

δ=0,67 (s,3H): 5-CH$_3$
δ=1,1 (s,3H): 5-CH$_3$
δ=1,5–2,1 (m,4H): H-1', H-2'
δ=3,5 (q,4H): H-4, H-6
δ=4,2–4,6 (m,2H): H-2, H-3'
δ=7,4; 7,9 (m,5H): Aromatic H's
δ=8,5 (d,1H): N<u>H</u>
δ=12 (bs,1H): COO<u>H</u>

EXAMPLE 8

In a manner analogous to Example 6 there were reacted 17.2 grams of 2-(2'-formylethyl)-5,5-dimethyl-1,3- dioxane. Instead of acetic anhydride there were used 9.8 grams of methyl chloroformate. Recrystallization from diisopropyl ether yielded 22.1 grams of N-methoxycarbonylglutamic acid-γ-semialdehyde-2,2-dimethylpropylene-1,3-acetal (Melting Point: 82°-83° C.).

| Elemental Analysis $C_{12}H_{21}NO_6$ | | |
|---|---|---|
| Calculated | C 52,35% | H 7,69% | N 5,09% |
| Found | C 52,58% | H 7,75% | N 5,04% |
| $^1$H—NMR—Spectrum (CDCl$_3$) | | |

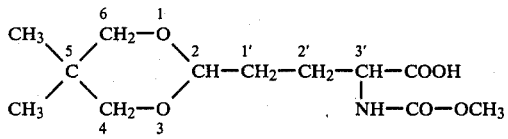

δ=0,7 (s,3H): 5-CH$_3$
δ=1,15 (s,3H): 5-CH$_3$
δ=1,4-2,1 (m,2H): H-1', H-2'
δ=3,5 (q,4H): H-4, H-6
δ=3,65 (s,3H): O-C<u>H</u>$_3$
δ=4,2-4,6 (m,2H): H-2, H-3'
δ=5,6 (d,1H): N<u>H</u>
δ=10,7 (s,1H: (COO<u>H</u>

EXAMPLE 9

A solution of 10.85 grams of N-acetylglutamic acid-γ-semialdehyde-ethylene-acetic (produced according to Example 3) in 100 ml of 0.1 N HCl and heated to 60° C. was dropped within one hour into a stirred solution of 7.3 grams of phenylhydrazine hydrochloride in 75 ml of 0.1 N HCl heated to 90° C. The reaction mixture was subsequently held for a further 2.5 hours at 90° C. After slowly cooling to 10° C. the precipitate formed was filtered off, washed with water and dried at reduced pressure. The yield of N-acetyl-D,L-tryptophane was 8.2 grams (66% of theory).

EXAMPLE 10

A solution of 11.5 grams of N-acetyl-glutamic acid-γ-semialdehyde-propylene-1,3-acetal and 7.3 grams of phenylhydrazine hydrochloride in 175 ml of 0.1 N HCl was heated for 3 hours at 90° C. with vigorous stirring. After slowly cooling down to 10° C. the precipitate formed was filtered off and dried at reduced pressure. The yield of N-acetyl-D,L-tryptophane was 7.6 grams (62% of theory).

EXAMPLE 11

In a manner analogous to Example 10 12.95 grams of N-acetyl-glutamic acid-γ-semialdehyde 2,2-dimethyl-propylene-1,3-acetal and 7.3 grams of phenylhydrazine hydrochloride were converted to N-acetyl-D,L-tryptophane. The yield was 8.5 grams (69% of theory).

EXAMPLE 12

A solution of 7.5 grams of N-benzoylglutamic acid-γ-semialdehyde-ethylene-acetal in 100 ml of 0.3 N HCl at 65° C. was dropped into a stirred solution heated to 90° C. of 4.1 grams of phenylhydrazine hydrochloride in 0.1 N HCl (100 ml) within one hour and held at 90° C. for a further 3 hours. An oily phase separated out, which crystallized to a friable mass during cooling. Recrystallization from 80 ml of 25% aqueous acetic acid yielded 6.2 grams of N-benzoyl-D,L-tryptophane. (72% of theory).

EXAMPLE 13

In a manner analogous to Example 12 7.3 grams of N-benzoylglutamic acid-γ-semialdehyde propylene-1,3-acetal from Example 5 and 3.6 grams of phenylhydrazine hydrochloride were converted into 5.8 grams of N-benzoyl-D,L-tryptophane (75% of theory).

EXAMPLE 14

In a manner analogous to Example 12 8 grams of N-benzoylglutamic acid-γ-semialdehyde-2,2-dimethyl-propylene-1,3-acetal from Example 7 and 3.6 grams of phenylhydrazine hydrochloride were converted into 5.4 grams of N-benzoyl-D,L-tryptophane (70% of theory).

The entire disclosure of German priority application P 3043252.1-42 is hereby incorporated by reference.

What is claimed is:

1. A cyclic acetal of N-acylglutamic acid-γ-semialdehyde of the formula

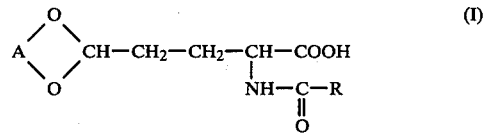

(I)

in which A is an alkylene group with 2 to 3 carbon atoms or such an alkylene group substituted by 1 to 3 methyl groups and R is a methyl, methoxy, phenyl, or benzyloxy group.

2. A cyclic acetal according to claim 1 where R is methyl.

3. A cyclic acetal according to claim 1 where R is methoxy.

4. A cyclic acetal according to claim 1 where R is phenyl.

5. A cyclic acetal according to claim 1 where R is benzyloxy.

* * * * *